United States Patent [19]

Koch et al.

[11] 4,283,390

[45] Aug. 11, 1981

[54] ANTIBIOTICS AND PROCESS FOR PRODUCTION THEREOF

[75] Inventors: Kay F. Koch, North Salem; Ralph E. Kastner, Indianapolis, both of Ind.

[73] Assignee: Eli Lilly and Company, Indianapolis, Ind.

[21] Appl. No.: 90,386

[22] Filed: Nov. 1, 1979

[51] Int. Cl.$^3$ .............................................. A61K 35/00
[52] U.S. Cl. ..................................... 424/122; 424/115; 435/169
[58] Field of Search ................. 424/122, 115; 435/169

[56] References Cited

U.S. PATENT DOCUMENTS 3,769,418  10/1973  Prelog et al. ........................ 424/121

OTHER PUBLICATIONS

Hutter et al., Helve. Chim. Act 50, pp. 1533-1539 (1967).
Dunitz et al. Helve Chim. Act. 54, pp. 1709-1713 (1971).
Derwent Farmdoc, Abstracting Japan Pat. No. 76154B/42, Published 2-28-78.
Omura et al., The J. of Antibiotics, 31, pp. 1091-1093 (1978).

Primary Examiner—Jerome D. Goldberg
Attorney, Agent, or Firm—Dwight E. Morrison; Arthur R. Whale

[57] ABSTRACT

Antibiotic A-39183 complex, comprising microbiologically active, related factors A, B, C, D, and E, is produced by submerged, aerobic fermentation of a new microorganism Streptomyces sp., NRRL 12049. The A-39183 antibiotics are closely related antibiotics. The individual A-39183 factors are separated by chromatography. The A-39183 factors are antibacterial agents which have activity against Staphylococcus and Streptococcus species that are penicillin resistant. The A-39183 factors are also active against both gram-positive and gram-negative anaerobic bacteria, and are ionophores.

6 Claims, 5 Drawing Figures

ANTIBIOTICS AND PROCESS FOR PRODUCTION THEREOF

BACKGROUND OF THE INVENTION

1. Field of the Invention

This invention relates to a group of antibiotics which have activity against certain Staphylococcus species and Streptococcus species which are resistant to penicillin. Staphylococcus species, for example cause pneumonia, meningitis, boils, carbuncles, abcesses, and other suppurative inflammations.

Streptococcus species are found associated in a great variety of pathologic conditions among which are gangrene, puerperal infections, subacute bacterial endocarditis, septic sore throat, rheumatic fever, and pneumonia. Agents which are active against Staphylococcus and Streptococcus species are, therefore, greatly needed.

2. Description of the Prior Art

In the prior art is U.S. Pat. No. 3,769,418 (Oct. 30, 1973), which discloses the production of Antibiotic A-28829, also known as boromycin. See also Hutter et al., *Helvetica Chimica Acta* 50, 1533-1539 (1967) concerning the production of boromycin. The structure of boromycin is reported by Dunitz et al., *Helvetica Chimica Acta* 54, 1709-1713 (1971). Boromycin is sometimes produced in small quantities by Streptomyces species NRRL 12049.

SUMMARY OF THE INVENTION

This invention relates to an antibiotic complex comprising several factors, including individual factors A, B, C, D, and E. This complex is produced by culturing a hitherto undescribed microorganism Streptomyces sp. NRRL 12049. These A-39183 antibiotics inhibit the growth of certain pathogenic microorganisms, in particular those within the gram-positive genera Staphylococcus and Streptococcus, as well as gram-negative anaerobic organisms of the genus Bacteroides and also a number of gram-positive anaerobic organisms.

DESCRIPTION OF THE DRAWINGS

Infrared absorption spectra of A-39183 factors A, B, C, D and E are presented in the drawings as follows.

DETAILED DESCRIPTION OF THE INVENTION

Figure 1:
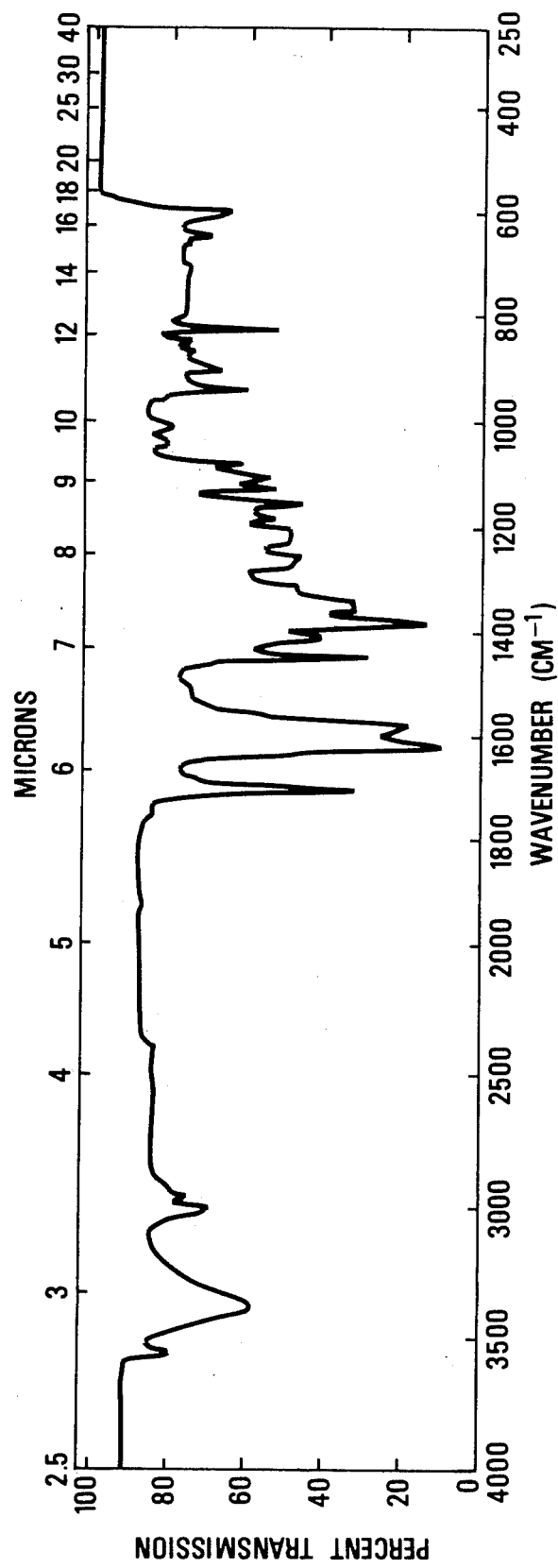
FIG. 1—A-39183 factor A (in chloroform)

This invention relates to antibiotic substances. In particular, it relates to an antibiotic complex comprising several factors, including individual factors A, B, C, D, and E. This complex is produced by culturing a hitherto undescribed microorganism, Streptomyces sp. NRRL 12049.

The term "complex", as used in the fermentation art and in this specification, refers to a mixture of co-produced individual antibiotic factors. As will be recognized by those familiar with antibiotic production by fermentation, the number and ratio of the individual factors produced in an antibiotic complex will vary, depending upon the fermentation conditions and the strain used.

The A-39183 complex is produced by culturing Streptomyces sp. NRRL 12049, or an A-39183-producing variant or mutant thereof, under submerged aerobic fermentation conditions until a substantial level of antibiotic activity is produced. Most of the antibiotic activity is generally found associated with the mycelium, while minor amounts of antibiotic activity may be present in the broth. The A-39183 complex is most readily separated from the fermentation mixture by removal of the fermentation broth by filtration. The filtrate is generally discarded. The filter cake is extracted with a suitable solvent such as methanol or acetone. The extract is concentrated to remove the organic solvent, leaving behind an aqueous concentrate containing the crude A-39183 complex. The A-39183 complex can be further purified and separated into its individual factors by chromatographic techniques.

The antibiotic substances of this invention are arbitrarily designated herein as A-39183 antibiotics. The A-39183 complex contains several individual factors which are designated A-39183 factors A, B, C, D, and E. In discussions of utility, the term "A-39183 antibiotic" will be used, for the sake of brevity, to denote a member selected from the group consisting of A-39183 complex, and A-39183 factors A, B, C, D, and E.

The A-39183 factors of this invention are structurally related to each other. As many as five antibiotic factors are recovered from the fermentation and are obtained as a mixture, the A-39183 complex. It will be recognized that the ratio of the factors in the A-39183 complex will vary, depending upon the fermentation conditions used. In general, however, A-39183 factor B is a major component of the complex, accounting for approximately 46% of the complex. A-39183 factor A is present in amounts of approximately 36%. A-39183 factors C, D and E are minor factors, together accounting for approximately 18% of the A-39183 complex. The individual factors A, B, C, D, and E are separated and isolated as individual compounds as hereinafter described. The A-39183 complex is soluble in acetone, ethyl acetate, chloroform, dimethylformamide, dimethyl sulfoxide, trifluoroethanol, the lower alkanols such as methanol, sparingly soluble in benzene and toluene, and insoluble in water.

The following paragraphs describe the physical and spectral properties of the A-39183 factors which have thus far been characterized.

A-39183 FACTOR A

Antibiotic A-39183 factor A is a yellow, crystalline solid, having a molecular weight of 598.58, as determined by mass spectrometry, and an approximate elemental analysis as follows: 67.95% carbon, 5.20% hydrogen, and 26.79% oxygen. Based on elemental analysis and molecular weight, an empirical formula of $C_{34}H_{30}O_{10}$ is assigned to factor A. Electrometric titration of factor A in 66% dimethylformamide in water indicated the presence of two titratable groups having $pK_a$ values of about 6.75 and 8.43 (initial pH 4.81). A-39183 factor A has the following specific rotation: $[\alpha]_D^{25} + 18.9°$ (c 9.52, trifluoroethanol).

The infrared absorption spectrum of A-39183 factor A in chloroform is shown in the accompanying drawings as FIG. 1. The following distinguishable absorption maxima are observed: 3560, 3380 (very broad), 3000, 2960, 2930, 1705, 1620, 1580, 1510, 1447, 1410, 1380, 1350, 1340, 1312, 1270, 1256, 1182, 1154, 1123, 1102, 1079, 1040, 1007, 950, 936, 900, 868, 845, 822, 643, and 598 cm$^{-1}$.

The ultraviolet absorption maxima of the A-39183 factors, including factor A, in methanol under acid, neutral and basic conditions are summarized in Table 1.

TABLE 1

UV Spectrophotometry of A-39183 Factors

| Factor | Acidic or Neutral $\lambda_{max}$ nm($\epsilon$) | Basic $\lambda_{max}$ nm($\epsilon$) |
|---|---|---|
| A | 227 (52,200) | 230 (59,200) |
|   | 269 (69,200) | 266 (58,000) |
|   | 300(s)* (7,200) |  |
|   | 312 (6,200) |  |
|   | 328 (6,800) | 340 (15,000) |
|   | 408 (16,200) | 423 (24,800) |
| B | 228 (57,400) | 228 (61,000) |
|   | 266 (48,000) | 266 (42,000) |
|   | 325(s) (8,000) | 340 (14,200) |
|   | 420 (15,000) | 426 (19,400) |
| C | 226 (44,200) | 229 (50,100) |
|   | 268 (55,600) | 266 (49,200) |
|   | 300(s) (6,200) |  |
|   | 310(s) (5,300) |  |
|   | 327 (5,300) | 328(s) (11,000) |
|   |  | 340 (11,900) |
|   | 410 (13,800) | 420 (17,000) |
| D | 226 (36,900) | 228 (31,000) |
|   | 269 (40,800) | 266 (38,200) |
|   | 324(s) (7,500) | 335 (10,600) |
|   | 410 (10,800) | 420 (16,500) |
| E | 226 (18,900) | 230(s) (23,800) |
|   | 269 (18,600) | 264 (20,400) |
|   | 320(s) (4,800) | 325(s) (7,300) |
|   | 405 (4,600) | 412 (7,500) |

*(s) = shoulder

Antibiotic A-39183 factor A is soluble in acetone, ethyl acetate, chloroform, dimethylformamide, dimethyl sulfoxide, and trifluoroethanol.

The X-ray crystallographic unit cell parameters for A-39183 factor A are set forth in Table 2, which follows.

TABLE 2

A-39183 Factor A Crystallographic Parameters $C_{34}H_{30}O_{10}$   M.W. 598.58 a = 16.378 ± 0.002 Å
b = 15.173 ± 0.004 Å
c = 12.250 ± 0.002 Å
SPACE GROUP: P $2_1 2_1 2_1$ (19)
Z = 4
$\rho_{obs}$ = 1.34 g. cm.$^3$
$\rho_{calc.}$ = 1.31 g. cm.$^3$ The X-ray powder diffraction characteristics of A-39183 factor A, determined on a sample recrystallized from a mixture of methanol and chloroform (copper radiation, 1.5418λ, nickel filter, d=interplanar spacing in angstroms) are recorded in Table 3, which follows.

TABLE 3

X-Ray Diffraction Characteristics of Antibiotic A-39183 Factor A

| Spacing d(Å) | Relative Intensities I/I$_1$ |
|---|---|
| 11.12 | 0.50 |
| 9.46 | 1.00 |
| 8.15 | .17 |
| 7.08 | .08 |
| 6.87 | .29 |
| 6.02 | .21 |
| 5.59 | .08 |
| 5.35 | .08 |
| 5.01 | .21 |

TABLE 3-continued

X-Ray Diffraction Characteristics of Antibiotic A-39183 Factor A

| Spacing d(Å) | Relative Intensities I/I$_1$ |
|---|---|
| 4.63 | .25 |
| 4.41 | .29 |
| 4.08 | .13 |
| 3.90 | .08 |
| 3.75 | .13 |
| 3.52 | .13 |
| 3.47 | .17 |
| 3.29 | .04 |
| 3.16 | .17 |
| 3.09 | .21 |
| 3.02 | .04 |
| 2.81 | .13b* |
| 2.68 | .08 |
| 2.58 | .04 |
| 2.49 | .04 |

*b = broad

On the basis of X-ray diffraction analysis and the observed physical data, the structure of A-39183 factor A is believed to be as follows:

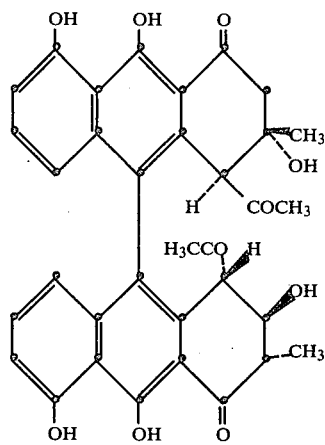

A-39183 FACTOR B

Antibiotic A-39183 factor B is a red, crystalline solid having a molecular weight of 580, as determined by mass spectrometry, and an approximate elemental analysis as follows: 70.56% carbon, 4.97% hydrogen, and 24.57% oxygen. Based on elemental analysis and molecular weight, an empirical formula of $C_{34}H_{28}O_9$ is assigned to factor B. Electrometric titration of factor B in 66% dimethylformamide in water indicated the presence of two titratable groups at pK$_a$ values of about 6.68 and 8.42 (initial pH 4.03). A-39183 factor B has the following specific rotation: $[\alpha]_D^{25} +576.9°$ (c8.85, trifluoroethanol).

Figure 2:
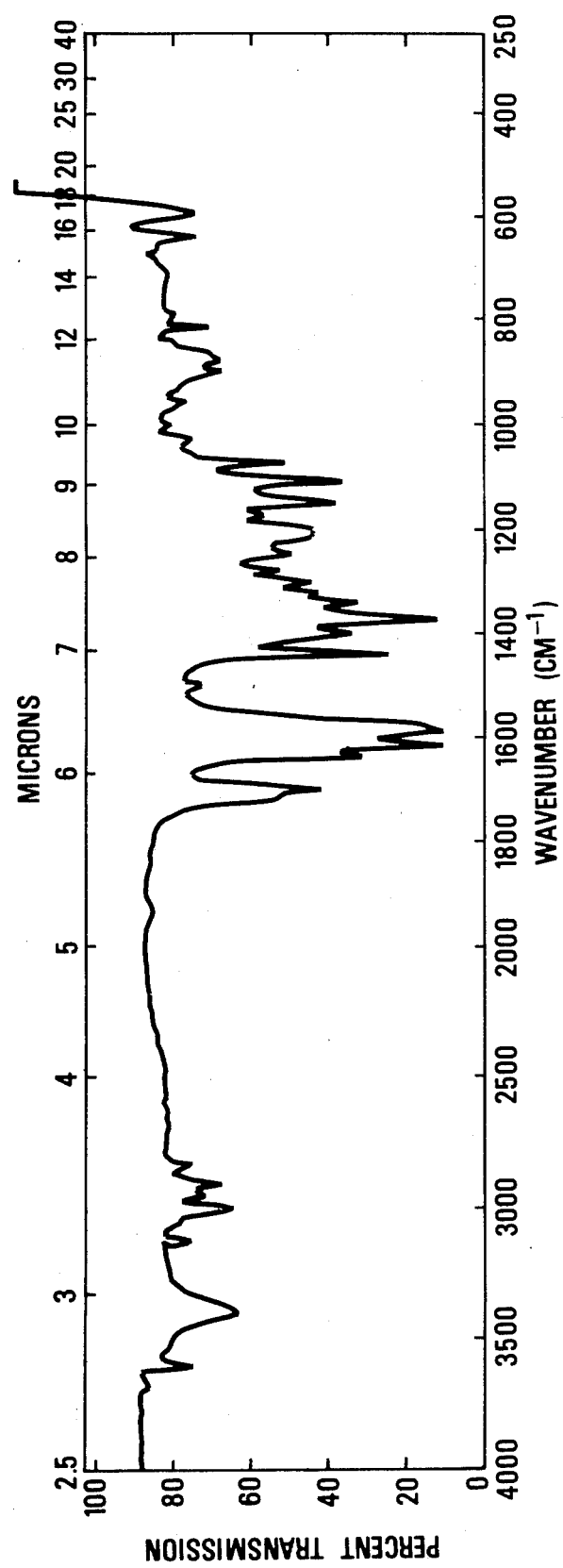
FIG. 2—A-39183 factor B (in chloroform)

The infrared absorption spectrum of A-39183 factor B in chloroform is shown in the accompanying drawings as FIG. 2. The following distinguishable absorption maxima are observed: 3605, 3400 (very broad), 3130, 3000, 2955, 2905, 2840, 1935, 1710, 1700, 1633, 1614, 1588, 1580, 1498, 1438, 1398, 1370, 1340, 1322, 1302, 1278, 1243, 1182, 1148, 1108, 1072, 1030, 998, 955, 897, 875, 812, 788, 640, and 594 cm$^{-1}$.

The ultraviolet absorption maxima of A-39183 factor B in both neutral, acidic, and basic methanol are recorded in Table 1.

Antibiotic A-39183 factor B is soluble in the same solvents as factor A.

The X-ray powder diffraction characteristics of A-39183 factor B, determined on a sample recrystallized from toluene (copper radiation, 1.5418Å, nickel filter, d=interplanar spacing in angstroms) are recorded in Table 4, which follows.

TABLE 4
X-Ray Diffraction Characteristics of Antibiotic A-39183 Factor B

| Spacing d(Å) | Relative Intensities I/I$_1$ |
|---|---|
| 9.21 | .72 |
| 8.19 | 1.00 |
| 7.31 | .22 |
| 6.76 | .11 |
| 5.73 | .22 |
| 5.39 | .28b* |
| 4.90 | .61 |
| 4.73 | .56 |
| 4.48 | .39 |
| 4.21 | .28 |
| 4.04 | .22 |
| 3.74 | .11 |
| 3.66 | .33 |
| 3.55 | .28 |
| 3.43 | .33 |
| 3.29 | .11 |
| 3.14 | .22 |
| 2.94 | .06b |
| 2.76 | .11 |
| 2.63 | .06 |
| 2.59 | .06 |
| 2.45 | .11 |

*b = broad

Based upon observed physical data and upon structure elucidation studies, the following structure is assigned to antibiotic A-39183 factor B:

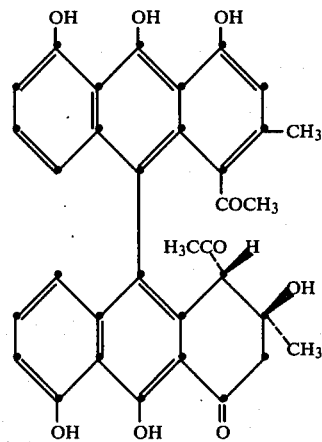

Antibiotic A-39183 factor B appears to be identical with an antibiotic named setomimycin, produced by a strain of Streptomyces identified as *Streptomyces pseudovenezuelae*, and recently reported by Omura et al., *The Journal of Antibiotics*, 31, 1091-1098 (1978).

A-39183 FACTOR C

Antibiotic A-39183 factor C is a yellow, crystalline solid having a molecular weight of about 598, as determined by mass spectrometry, and an approximate elemental analysis as follows: 68.03% carbon, 4.78% hydrogen, and 26.58% oxygen. Based on elemental analysis and molecular weight, an empirical formula of $C_{34}H_{30}O_{10}$ is assigned to factor C. A-39183 factor C has the following specific rotation: $[\alpha]_D^{25}$ −14.89° (C 1.75, methanol).

Figure 3:
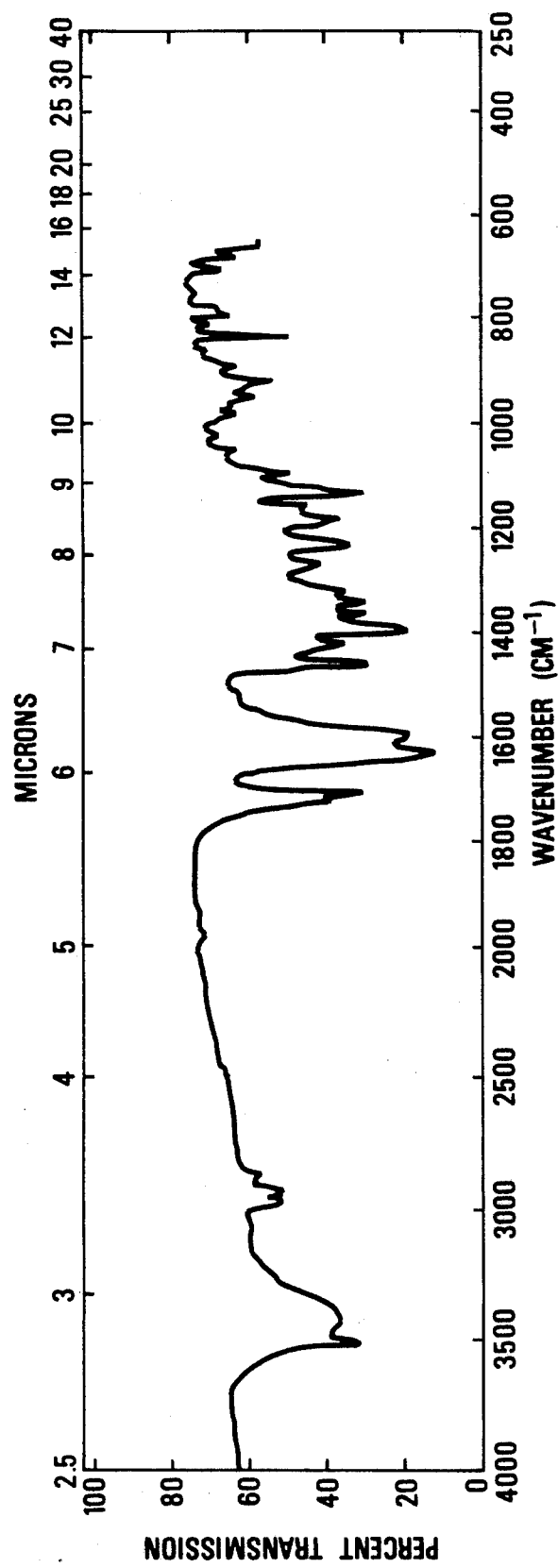
FIG. 3—A-39183 factor C (in KBr pellet)

The infrared absorption spectrum of A-39183 factor C in KBr pellet is shown in the accompanying drawings as FIG. 3. The following significant absorption maxima are observed: 3498, 3420, 2970, 2930, 2861, 1971, 1717, 1701, 1623, 1599, 1585, 1452, 1414, 1357, 1335, 1312, 1261, 1223, 1172, 1151, 1122, 1086, 1041, 1011, 980 (shoulder), 970, 955, 938, 905, 879, 870 (shoulder), 851, 801, 781, 750 (shoulder), 740, 692, and 666 cm$^{-1}$.

The ultraviolet absorption maxima of antibiotic A-39183 factor C in methanol under acid, neutral, and basic conditions are summarized in Table 1.

Antibiotic A-39183 factor C is soluble in acetone, ethyl acetate, dimethylformamide, dimethyl sulfoxide, trifluoroethanol, the lower alkanols such as methanol, sparingly soluble in benzene and toluene, and insoluble in water.

The structure of antibiotic A-39183 factor C has not yet been determined. However, the data set forth hereinbefore suggests a structure similar to that of factor A.

A-39183 FACTOR D

Figure 4:
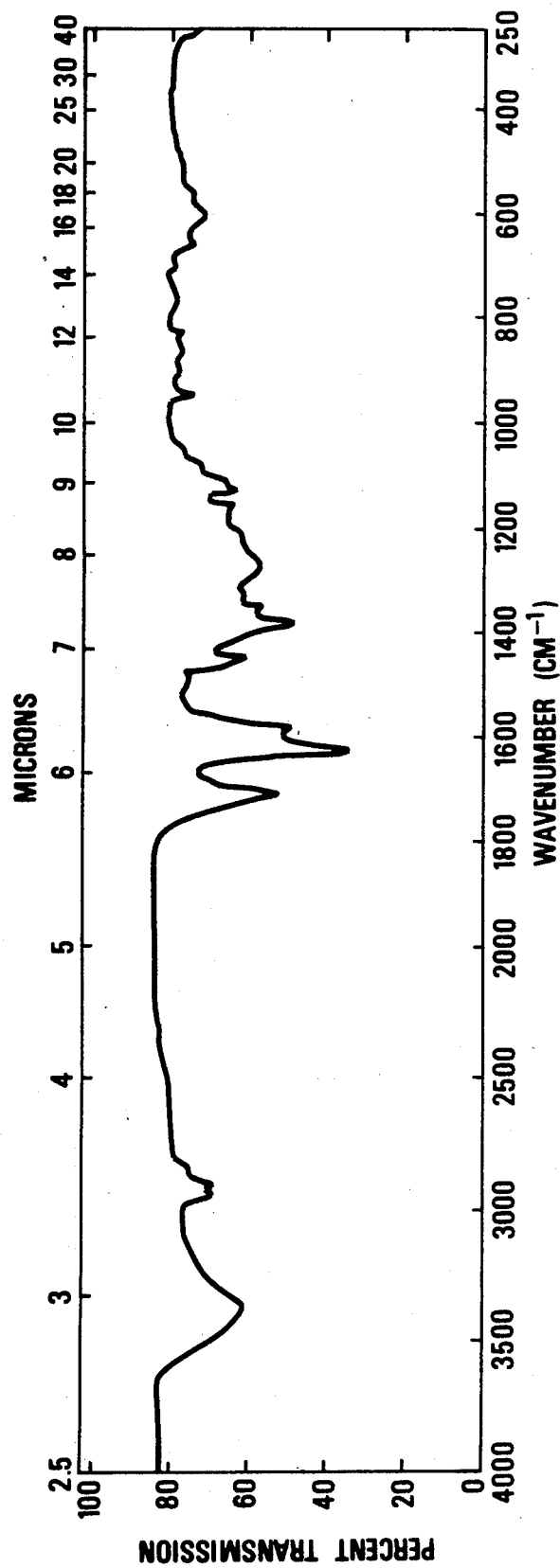
FIG. 4—A-39183 factor D (in KBr pellet)

Antibiotic A-39183 factor D is a yellow-brown, amorphous solid. The infrared absorption spectrum of A-39183 factor D in KBr pellet is shown in the accompanying drawings as FIG. 4. The following significant absorption maxima are observed: 3365 (broad), 2940, 2910, 2835, 2815 (shoulder), 1708, 1622, 1581 (shoulder), 1447, 1380, 1354, 1330, 1270, 1210 (shoulder), 1126, 1110 (shoulder), 1076 (shoulder), 1047 (shoulder), 943, 905, 892, 860, 823, 760, 703, 656, 601, and 560 cm$^{-1}$.

A-39183 FACTOR E

Figure 5:
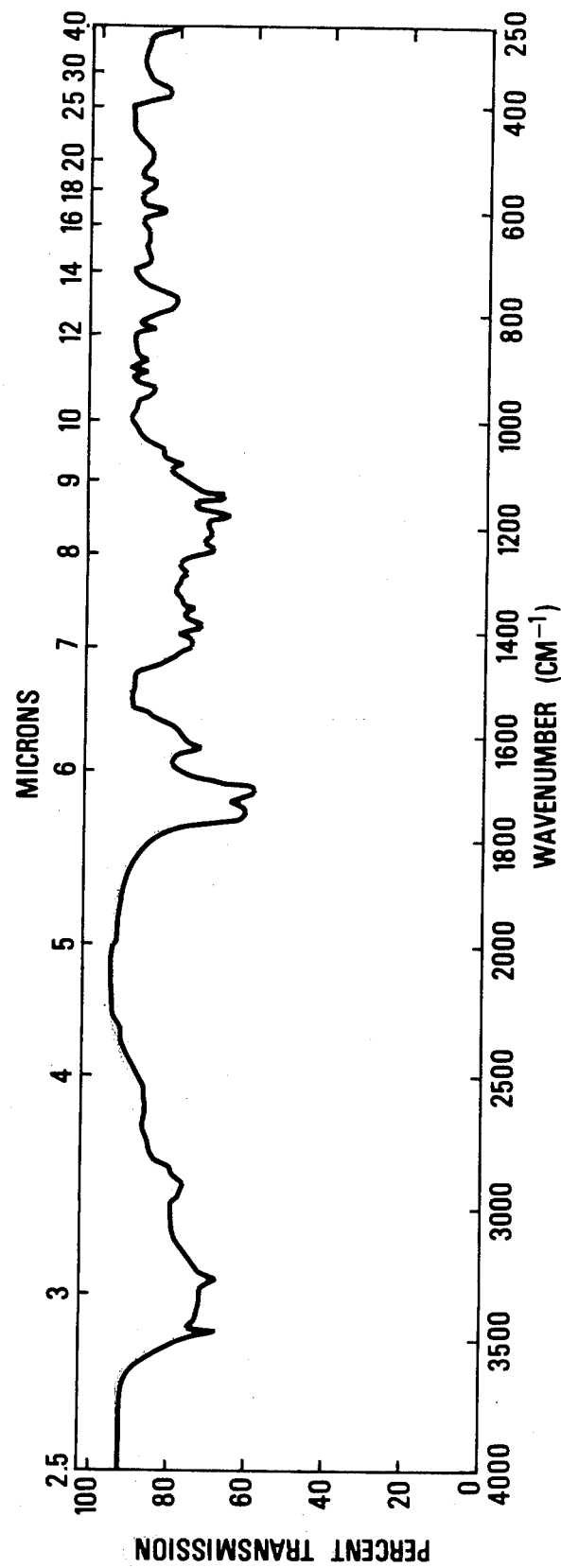
FIG. 5—A-39183 factor E (in KBr pellet).

Antibiotic A-39183 factor E is a brown, amorphous solid. The infrared absorption spectrum of A-39183 factor E in KBr pellet is shown in the accompanying drawings as FIG. 5. The following significant absorption maxima are observed: 3471, 3267, 2945, 2907, 2850 (shoulder), 1745, 1705, 1623, 1423, 1388, 1355, 1335 (shoulder), 1303 (shoulder), 1289, 1242, 1212, 1177, 1142, 1081, 1053 (shoulder), 940, 905, 872, 822, 764, 690, 599, 549, 504, 484, and 375 cm$^{-1}$.

The approximate $R_f$ values of A-39183 factors A–E, using silica gel [Quantum LQD (Whatman, Inc., Clifton, N.J. 07014) treated with 0.5 N citric acid] thin-layer chromatography (TLC), a toluene:acetone (3:1) solvent system, and visual inspection and *B. subtilis* bioautography, are given in Table 5:

TABLE 5

| A-39183 Factor | $R_f$ Value |
|---|---|
| A | 0.53 |
| B | 0.68 |
| C | 0.46 |
| D | 0.35 |
| E | 0.28 |

The A-39183 antibiotics of this invention inhibit the growth of certain pathogenic microorganisms, in particular those within the gram-positive genera Staphylococcus and Streptococcus. The A-39183 antibiotics also inhibit the growth of gram-negative anaerobic organisms of the genus Bacteroides, as well as the growth of a number of gram-positive anaerobic organisms.

The Streptomyces sp. culture which is useful for the production of the A-39183 antibiotics and which was initially isolated from a mixture of soil samples from Venezuela and Haiti, has been deposited and made a part of the stock culture collection of the Northern Regional Research Center, U.S. Department of Agriculture, Agricultural Research Service, Peoria, Ill., 61604, from which it is available to the public under the number NRRL 12049.

As is the case with other organisms, the characteristics of the A-39183-producing culture, Streptomyces sp. NRRL 12049, are subject to variation. For example, natural variants, mutants (spontaneous or induced), transconjugants and recombinants (including recombinant DNA on plasmids) of the NRRL 12049 strain, or derived from this strain, which produce the A-39183 antibiotics may be used in this invention.

A number of different media may be used with Streptomyces sp. NRRL 12049 to produce the A-39183 complex. For economy in production, optimal yield, and ease of product isolation however, certain culture media are preferred. Thus, for example, preferred carbon sources are glucose, starch, and dextrin. Optimum levels of carbon sources are from about 5 to about 10 percent by weight.

Preferred nitrogen sources are fish meal, soybean meal, cottonseed meal, peanut meal, and casein, or combinations of these nutrients. Meat solubles, peptone, corn meal, enzyme-hydrolyzed casein, and nitrate salts are also useful.

Molasses is utilized, not as a source of sucrose, which the culture does not use, but as a possible source of phosphate, calcium, iron, magnesium, manganese, aluminum, zinc, cobalt, sodium, as well as other ions which molasses is known to contain. Molasses increases the fermentation yields, probably due to the phosphate and/or minerals named above, or possibly due to amino acids or other unidentified components of the molasses.

Alternatively, the necessary nutrient salts can be incorporated into the culture media in the form of the customary soluble salts capable of yielding sodium, magnesium, calcium, ammonium, chloride, carbonate, phosphate, sulfate, nitrate and like ions.

Essential trace elements necessary for the growth and development of the organism should also be included in the culture medium. These trace elements commonly occur as impurities in other constituents of the medium in amounts sufficient to meet the growth requirements of the organism.

Addition to the fermentation medium of a polypropylene glycol having a molecular weight of from about 1200 to about 2000 increases the yield of the antibiotic by approximately 100 percent, and concurrently controls foaming. The glycol may be added to the fermentation medium prior to sterilization, or may be sterilized separately and added aseptically at a later time. Maximum benefit is obtained by early addition, preferably in the first 2 or 3 days of the fermentation. Later additions are progressively less beneficial. Optimum addition levels are at about 0.2–0.7% by volume.

For producing substantial quantities of the A-39183 antibiotics, submerged aerobic fermentation in tanks is preferred. However, small quantities of the A-39183 antibiotics may be obtained by shake-flask culture. For tank fermentation, it is preferable to use a vegetative inoculum. The vegetative inoculum is prepared by inoculating a small volume of culture medium with the spore form, mycelial fragments, or a lyophilized pellet of the organism to obtain a fresh, actively growing culture of the organism. The vegetative inoculum is then transferred to a larger tank where, after an appropriate incubation time, the A-39183 complex is produced in optimal yield.

The A-39183-producing organism can be grown over a broad temperature range of from about 20° to about 43° C. Optimum production of A-39183 antibiotic complex appears to occur at a temperature of about 30° C.

As is customary in aerobic submerged culture processes, sterile air is dispersed through the culture medium. For efficient growth of the organism, the volume of the air used in tank production is in the range of from about 0.05 to about 0.25 volumes of air per volume of culture medium per minute (v/v/m), and from about 100 to about 200 RPM agitation. An optimum rate in a 165-liter vessel is about 0.15 v/v/m, with agitation provided by a propeller rotating at about 190 RPM, which provides a dissolved oxygen level of 50–60% of air saturation at atmospheric pressure.

Production of the A-39183 antibiotics can be monitored during fermentation by either agar-diffusion or turbidimetric methods. Test organisms suitable for use include *Staphylococcus aureus, Bacillus subtilis,* and *Micrococcus luteus.* The bioassay is preferably performed employing *S. aureus* NRRL B-314 in a turbidimetric test.

Antibiotic activity is generally present after about 60 hours fermentation. Peak antibiotic production occurs at from about six to about eight days fermentation time.

The antibiotic activity is present both in broth samples from which the biomass has been removed, and in the biomass. The broth:biomass ratio of antibiotic activity varies spontaneously and in response to the fermentation conditions being used. However, the antibiotic activity present in the broth is consistently less than 50% of the total activity produced in the fermentation, is frequently less than 10%, and is occasionally less than 1%. The remainder of the antibiotic activity is, of course, in the biomass. The variation in distribution appears to be brought about, at least in part, by the vigor with which the fermentation mass is stirred or mixed during the fermentation.

The A-39183 antibiotics can be recovered from the fermentation medium by methods known in the art. For example, in the work-up of a large-scale tank fermentation the whole broth is filtered using a filter press. The minor amounts of the A-39182 antibiotic occurring in the filtered fermentation broth can be recovered using well-known extraction procedures employing water-immiscible solvents such as ethyl acetate, amyl acetate, and the like. However, the bioassay may indicate in any given fermentation that the amount of activity present in the filtered broth does not warrant its recovery. The filter cake is then extracted with a suitable solvent, such as methanol, acetone, or the like, with acetone being the solvent of choice. Usually, more than one extraction is done in order to recover the maximum amount of the A-39183 complex. The extracts are combined and concentrated, thus removing the acetone, and leaving behind an aqueous concentrate containing the crude A-39183 complex. This aqueous concentrate is extracted with ethyl acetate. The ethyl acetate extracts are combined and concentrated in vacuo to a small volume. The concentrate is diluted with fresh ethyl acetate and added to a large volume of hexane. The solid material which separates is filtered off to give antibiotic A-39183 complex.

Separation of the individual A-39183 factors from the A-39183 complex includes the use of additional adsorption and extraction procedures. Adsorptive materials such as silica gel, Florisil (magnesium silicate, Floridin Co., Tallahassee, Fla.), ion-exchange resins, and the like can be advantageously used. High-performance liquid chromatography (HPLC) is an especially preferred tool for separating the A-39183 individual factors.

The A-39183 antibiotics inhibit the growth of certain microorganisms. The levels at which the A-39183 antibiotics inhibit the growth of microorganisms were determined using various testing procedures.

DISC-PLATE SCREENING PROCEDURE

Agar plates, inoculated with the test organism, were used; 6 mm. discs (0.02 ml. capacity) were saturated from log 2 dilutions of the antibiotic solution. Disc content was 1/5 or 1/50 of the concentration of the solution used, i.e., disc content of 300 μg. or 30 μg. was obtained from a solution of 1500 μg./ml. concentration. The size of the zone of inhibition produced by the A-39183 antibiotics for each disc content is reported in the tables which follow.

AGAR-DILUTION SCREENING PROCEDURE

The agar-dilution procedure described by the International Collaborative Study (ICS) group was used to determine MIC values.

The results obtained from tests of antibiotic A-39183 factor A in the agar-dilution screening procedure are given in Table 6, which follows.

TABLE 6

| ACTIVITY OF A-39183 FACTOR A | |
|---|---|
| Test Organism | MIC (μg/ml)[1] |
| Staphylococcus aureus 3055* | 32 |
| Streptococcus faecalis X66 | 32 |

*benzylpenicillin-susceptible
[1]agar-dilution method

The results of both agar-dilution and disc-plate screening tests of antibiotic A-39183 factor B are given in Table 7, which follows.

TABLE 7

| ACTIVITY OF A-39183 FACTOR B | | | |
|---|---|---|---|
| | MIC | Zone Diameter (at μg/disc)[2] | |
| Test Organism | (μg/ml)[1] | 300 | 30 |
| Staphylococcus aureus 3055* | 0.5 | 0 | 0 |
| Staphylococcus aureus 3074** | 4.0 | 15.8 | 14.8 |
| Staphylococcus aureus 3130*** | — | 14.0 | 13.4 |
| Streptococcus faecalis X66 | 4.0 | — | — |
| Streptococcus pyogenes C203 | — | 10.0 | 8.0 |
| Streptococcus sp. (Group D) 9960 | — | 9.1 | 0 |
| Streptococcus pneumoniae Park I | — | 9.1 | 9.1 |

*benzylpenicillin-susceptible
**benzylpenicillin-resistant
***benzylpenicillin-resistant, methicillin-resistant
[1]agar-dilution method
[2]disc-plate method
— = not tested The A-39183 antibiotics are active against anaerobic bacteria. For example, the activity of Antibiotic A-39183 factors A and B is summarized in Table 8, which follows.

TABLE 8

| ACTIVITY OF A-39183 FACTORS-ANAEROBIC BACTERIA | | |
|---|---|---|
| Test Organism | Factor A | Factor B |
| Actinomyces israelii W855 | ≦0.5 | ≦0.5 |
| Clostridium perfringens 81 | 32 | 8 |
| Clostridium septicum 1128 | 16 | 2 |

TABLE 8-continued

| ACTIVITY OF A-39183 FACTORS-ANAEROBIC BACTERIA | | |
|---|---|---|
| Test Organism | Factor A | Factor B |
| Eubacterium aerofaciens 1235 | 32 | 8 |
| Peptococcus asaccharolyticus 1302 | 64 | 32 |
| Peptococcus prevoti 1281 | 32 | 8 |
| Peptostreptococcus anaerobius 1428 | 64 | 8 |
| Peptostreptococcus intermedius 1264 | 32 | 2 |
| Propionibacterium acnes 79 | 32 | 2 |
| Bacteroides fragilis 111 | 32 | ≦0.5 |
| Bacteroides fragilis 1877 | 32 | 1 |
| Bacteroides fragilis 1936B | 32 | 2 |
| Bacteroides thetaiotaomicron 1438 | 16 | 16 |
| Bacteroides melaninogenicus 1856/28 | >128 | >128 |
| Bacteroides melaninogenicus 2736 | 16 | 4 |
| Bacteroides vulgatis 1211 | 32 | 2 |
| Bacteroides corrodens 1874 | 32 | 1 |
| Fusobacterium symbiosum 1470 | 64 | 8 |
| Fusobacterium necrophorum 6054A | 16 | ≦0.5 |
| Bacteroides fragilis 1877 | —* | 4 |
| Bacteroides fragilis 103 | — | 4 |
| | | MIC (μg/ml) |
| Bacteroides fragilis 104 | — | 4 |
| Bacteroides fragilis 106 | — | 4 |
| Bacteroides fragilis 107 | — | 4 |
| Bacteroides fragilis 108 | — | 4 |
| Bacteroides fragilis 110 | — | 4 |
| Bacteroides fragilis 111 | — | 4 |
| Bacteroides fragilis 112 | — | 4 |
| Bacteroides fragilis 113 | — | 4 |
| Bacteroides fragilis 1451 | — | 4 |
| Bacteroides fragilis 1470 | — | 4 |
| Bacteroides fragilis 2 | — | 2 |
| Bacteroides fragilis 9 | — | 4 |
| Bacteroides fragilis 62 | — | 1 |
| Bacteroides corrodens 1874 | — | 4 |
| Bacteroides vulgatis 1563 | — | 8 |
| Bacteroides thetaiotaomicron 1438 | — | 4 |
| Bacteroides thetaiotaomicron 1900A | — | 16 |

*Not tested

The activity of Antibiotic A-39183 factor C against some gram-positive bacteria is reported in Table 9, which follows.

TABLE 9

| ACTIVITY OF A-39183 FACTOR C | | |
|---|---|---|
| | Zone Diameter (at μg/ml)[2] | |
| Test Organism | 1 | 5 |
| Staphylococcus aureus | tr[1] | 15 |
| Bacillus subtilis | tr | 13 |
| Bacillus subtilis[3] | 25 | 28 |

[1]tr = trace
[2]disc-plate method
[3]minimal medium

The A-39183 antibiotics are useful for suppressing the growth of Staphylococcus and Streptococcus organisms. These organisms grow on the surface of the skin, and the antibiotics could therefore be used, for example, in the treatment of acne. The A-39183 individual factors, or mixtures thereof in the purified state, can be formulated in pharmaceutically-acceptable diluents such as isopropyl alcohol for application to the skin. Such solutions can be made up with antibiotic concentrations of from about 1 to about 15 percent weight per volume. Alternatively, the antibiotics can be made up into creams or lotions for application to the skin.

The antibiotics of the A-39183 complex are ionophores, active in the transport of calcium ion, and capable of acting to partition magnesium and calcium ions from an aqueous phase to an organic phase. The antibiotics facilitate the uptake of iron ($Fe^{+2}$) ions into mitochondria that normally have a low uptake rate for $Fe^{+2}$ ions.

In order to illustrate more fully the operation of this invention, the following examples are provided.

EXAMPLE 1

A. Preparation of First Stage Inoculum

A medium was prepared for use in the agar slant culture of Streptomyces sp. NRRL 12049:

| Ingredient | Amount (g/L.) |
| --- | --- |
| Pre-cooked oatmeal | 60.0 |
| Yeast | 2.5 |
| $K_2HPO_4$ | 1.0 |
| KCl | 0.5 |
| $MgSO_4 . 7H_2O$ | 0.5 |
| $FeSO_4 . 7H_2O$ | 0.01 |
| Washed agar | 25.0 |
| Deionized water | q.s. to 1 liter. |

The pH of the medium was adjusted to 7.3 with aqueous sodium hydroxide before autoclaving; after autoclaving the pH was 6.7.

Spores of Streptomyces sp. NRRL 12049 were inoculated on a nutrient agar slant made up of the above-identified ingredients, and the thus inoculated slant was incubated for from about 7 to about 10 days at a temperature of about 30° C. The mature slant culture was covered with water and scraped with a sterile tool to loosen the spores and mycelium. The spores and mycelium were then suspended in calf serum and lyophilized to form a pellet. The pellet was used to inoculate 50 ml. of a medium having the following composition:

| Ingredient | Amount (g/L.) |
| --- | --- |
| Glucose | 10.0 |
| Sucrose | 20.0 |
| Beef extract | 5.0 |
| Peptone | 5.0 |
| Brewer's yeast | 5.0 |
| Enzyme-hydrolyzed casein | 5.0 |
| Calcium carbonate | 2.0 |
| Tap water | q.s. to 1 liter |

The inoculated medium was incubated in a 250 ml. wide-mouth Erlenmeyer flask at about 30° C. for about 48 hours on a shaker rotating through an arc 2 inches in diameter at 250 RPM.

This incubated medium is used either to inoculate small fermentors (the inoculum being approximately 1% per volume of medium) or to inoculate a second stage medium for the production of a larger volume of culture.

B. Preparation of Second Stage Inoculum

In order to provide a larger volume of inoculum, 2.5 ml. of incubated medium, prepared as described above, was used to inoculate 400 ml. of a second-stage growth medium having the same composition as that of the medium above. This second-stage medium was incubated in a wide-mouth 2-liter flask for about 24 hours at about 30° C. on a shaker rotating through an arc 2 inches in diameter at 250 RPM.

C. Fermentation of A-39183

Incubated second-stage medium (800 ml.) thus prepared was used to inoculate 100 liters of sterile production medium having the following composition:

| Ingredient | Amount (g/L.) |
| --- | --- |
| Silicone antifoam agent* | 0.2 |
| Glucose | 60.0 |
| Fish meal | 10.0 |
| Molasses, Blackstrap | 10.0 |
| $CaCO_3$ | 2.0 |
| $MgSO_4 . 7H_2O$ | 0.5 |
| Polypropylene glycol (2000) | 2.0 |
| Tap water | q.s. tp 100 liters |

*Dow-Corning Antifoam A.

The inoculated production medium was allowed to ferment in a 165-liter fermentation tank for about 7–8 days at a temperature of about 30° C. The fermentation medium was aerated with sterile air at the rate of 0.125 v/v/m and was stirred with conventional agitators at 190 RPM.

For the purpose of identifying the A-39183 factors produced in the fermentation, the following paper chromatography systems were used:

a. Whatman No. 1 paper was developed in water:methanol:acetone (12:3:1) adjusted to pH 10.5 with aqueous ammonium hydroxide, and then to pH 7.5 with aqueous hydrochloric acid. The approximate $R_f$ value of factor A is 0.5, and of factor B is 0.21.

b. Whatman No. 1 paper was developed in methanol:0.1 N aqueous hydrochloric acid (3:1). This system separates A-39183 factors A and B ($R_f$ 0.72) from boromycin ($R_f$ 0.86), which can be co-produced in the fermentation process.

EXAMPLE 2

Separation of A-39183 antibiotic complex

Whole fermentation broth (155 L.), obtained as described in Example 1, was filtered using a filter aid (Hyflo Supercel, a diatomaceous earth, Johns-Manville Products Corporation) in a filter press. The filtrate was discarded. The filter cake was extracted in the filter press two times with acetone. The two acetone extracts (41 L. and 45 L., respectively) were combined and concentrated to about 20 L. The concentrate was extracted two times with 10 L. portions of ethyl acetate. These ethyl acetate extracts were combined and concentrated to a volume of about 1.6 L. The concentrate, which contained a solid, was diluted to about 2.2 L. with ethyl acetate and was added to 22 L. of hexane. The A-39183 complex which precipitated as a solid was collected by filtration. It weighed 254 g.

Further purification of the A-39183 complex and separation of the factors was accomplished using a silica-gel column. The column was prepared by slurrying 20 L. of grade 62 silica gel (Grace) with 40 L. of 0.5 N citric acid in ethanol. The ethanol was removed by decantation, and the silica gel was washed twice with 40 L. portions of toluene. The silica gel was then packed in a column and washed with 40 L. of toluene.

A-39183 complex, 175 g., was dissolved in 1,750 ml. of chloroform and loaded onto the 20 L. silica-gel column. The column was washed with 40 L. of toluene and eluted successively with 80 L. of toluene:acetone (9:1), 80 L. of toluene:acetone (4:1), and 80 L. of toluene:acetone (3:1). Fractions of 2 L. each were collected. Fractions 1–10 were discarded.

Fractions 11–15, inclusive, were combined and concentrated in vacuo to yield solid materials which were then dissolved in toluene (100 mg.ml). The solid material which crystallized from this solution was identified as semi-pure factor B. The first crop weighed 21.4 g.; the second crop 10.7 g. Total weight 32.1 g.

Fractions 16-20, inclusive, were combined and concentrated in vacuo to a volume of about 100 ml. On cooling, factor A crystallized and was collected by filtration to yield 0.3 g. The filtrate was added to 1 L. of hexane. A mixture of A-39183 factors (2.5 g.) precipitated and was collected by filtration.

Fractions 21-39, inclusive, were combined and concentrated to a volume of about 200 ml. The solid which precipitated was separated by filtration to give 20.4 g. of factor A. The filtrate was further concentrated to give an additional 5.1 g. of factor A.

Fractions 51-56, inclusive, were combined and concentrated to a volume of about 100 ml. The solid which precipitated was separated by filtration to give 2.6 g. of factor C.

Fractions 57-70, inclusive, were combined and concentrated to yield an oil. This oil was dissolved in ethyl acetate and added to 10 volumes of hexane. A precipitate was separated by filtration to give 9.3 g. of factor D.

Fractions 71-76, inclusive, were discarded.

Fractions 77-90, inclusive, were combined and concentrated to yield an oil. This oil was dissolved in ethyl acetate and was added to 10 volumes of hexane. A precipitate which formed was separated by filtration to give 1.4 g. of factor E.

EXAMPLE 3

Purification of Antibiotic A-39183 Factor A

Crude antibiotic A-39183 factor A, 2.041 g., prepared as described in Example 2, was dissolved in 40 ml. of chloroform with the aid of some sonication. To the solution there was added 120 ml. of methanol, and the solution was heated on the steam bath until the volume was reduced to about 100 ml. by evaporation of the solvents. The solution was allowed to stand overnight at room temperature, during which time crystallization occurred. The dark supernatant mother liquor was decanted from the crystals. The crystals were rinsed with a small amount of methanol and dried. The crystals weighed 1.174 g.

The mother liquor gave a second crop of 134.0 mg. and a third crop of 519.2 mg.

EXAMPLE 4

Purification of Antibiotic A-39183 Factor B

Crude antibiotic A-39183 factor B, 306 mg., was dissolved in toluene (about 3 ml.) and allowed to stand at room temperature. After about 30 minutes, crystals had appeared. The crystals were recovered by filtration, washed with about 2.5 ml. of toluene, and dried. Weight=250.0 mg.

EXAMPLE 5

Purification of Antibiotic A-39183 Factor C

Crude factor C, prepared as described in Example 2, was purified by high performance liquid chromatography (HPLC) employing silica gel (Quantum LP-1, Whatman, Inc., Clifton, N.J.).

The silica gel was treated with 0.5 N citric acid in absolute ethanol. A column measuring 2 cm.×30 cm. (volume approx. 90 ml.) was filled with the thus-treated silica gel.

A suspension was prepared of 500 mg. of crude antibiotic A-39183 factor C in toluene, to which a small amount of acetone was added, and placed on the column.

The column was then eluted with a gradient mixture of toluene (1 L.) to toluene:acetone (3:1;1 L.). Fractions measuring 15 ml. in volume were collected each minute.

Fractions were monitored by TLC on Quantum silica plates in toluene:acetone (3:1) with 10 μg. spotted for proper visualization.

We claim:

1. Antibiotic A-39183 factor C, which is a yellow, crystalline solid having the following characteristics:
   (a) an approximate elemental composition of 68.03 percent carbon, 4.78 percent hydrogen, and 26.58 percent oxygen;
   (b) a molecular weight of about 598, as determined by mass spectrometry;
   (c) an infrared absorption spectrum with the following significant absorption maxima ($cm^{-1}$): 3498, 3420, 2970, 2930, 2861, 1971, 1717, 1701, 1623, 1599, 1585, 1452, 1414, 1357, 1335, 1312, 1261, 1223, 1172, 1151, 1122, 1086, 1041, 1011, 980 (shoulder), 970, 955, 938, 905, 879, 870 (shoulder), 851, 801, 781, 750 (shoulder), 740, 692, and 666;
   (d) ultaviolet absorption spectra in acidic or neutral methanol with absorption maxima at 226 nm ($\epsilon$44,200), 268 nm ($\epsilon$55,600), 300 nm (s) ($\epsilon$6,200), 310 (s), ($\epsilon$5,300), 327 nm ($\epsilon$5,900), and 410 nm ($\epsilon$13,800); and in basic methanol with absorption maxima at 229 nm ($\epsilon$50,100), 226 nm ($\epsilon$49,200), 328 nm (s) ($\epsilon$11,000), 340 nm ($\epsilon$11,900), and 420 nm ($\epsilon$17,000);
   (e) is soluble in acetone, ethyl acetate, dimethylformamide, dimethyl sulfoxide, trifluoroethanol, the lower alkanols, is sparingly soluble in benzene and toluene, and insoluble in water; and
   (f) an $R_f$ value of approximately 0.46 on silica-gel thin layer chromatography using a toluene:acetone (3:1) solvent system.

2. The A-39183 complex which is produced by cultivating Streptomyces sp. NRRL 12049 in a culture medium containing assimilable sources of carbon, nitrogen, and inorganic salts under submerged aerobic fermentation conditions until a substantial amount of antibiotic activity is produced.

3. The method of producing the A-39183 antibiotic complex which comprises cultivating Streptomyces sp. NRRL 12049 in a culture medium containing assimilable sources of carbon, nitrogen, and inorganic salts under submerged aerobic fermentation conditions until a substantial amount of antibiotic activity is produced.

4. The method of claim 3 wherein the fermentation is carried out in the presence of from about 0.2 to about 0.7 percent by volume of the fermentation medium of a polypropylene glycol having a molecular weight of from about 1200 to about 2000.

5. The method of claim 3 which includes the additional step of isolating the A-39183 antibiotic complex from the culture medium.

6. The method of claim 5 which includes the additional step of isolating A-39183 factor C from the separated A-39183 complex.

* * * * *